United States Patent [19]

Hicho

[11] Patent Number: 5,115,671
[45] Date of Patent: May 26, 1992

[54] METHOD AND APPARATUS FOR ANALYZING ROTATING MACHINES

[75] Inventor: Michael D. Hicho, Broadview Heights, Ohio

[73] Assignee: Life Systems, Inc., Cleveland, Ohio

[21] Appl. No.: 552,421

[22] Filed: Jul. 13, 1990

[51] Int. Cl.⁵ ............................................. G01P 15/00
[52] U.S. Cl. ........................................ 73/488; 73/660
[58] Field of Search ................ 73/488, 496, 506, 507, 73/570, 660; 340/670, 671, 683

[56] References Cited

U.S. PATENT DOCUMENTS

| | | | |
|---|---|---|---|
| 3,815,426 | 6/1974 | Rohner | 73/488 |
| 4,406,165 | 9/1983 | Coussineux | 73/488 |
| 4,426,641 | 1/1984 | Kurihara et al. | 340/683 |
| 4,452,079 | 6/1984 | Tiller | 73/506 |

FOREIGN PATENT DOCUMENTS 257126  5/1986  Fed. Rep. of Germany.

OTHER PUBLICATIONS

Estimation of the Surface Roughness on the Race or Balls of Ball Bearings by Vibration Analysis; Kanai et al., Transactions of the ASME 60/vol. 109, Jan. 1987.

*Primary Examiner*—Hezron E. Williams
*Assistant Examiner*—Louis M. Arana
*Attorney, Agent, or Firm*—Fay, Sharpe, Beall, Fagan, Minnich & McKee

[57] ABSTRACT

A vibration transducer (22) is mounted to a rotating machine (20) for sensing vibration thereof. An output electrical signal from the vibration transducer is analyzed to generate a level display (18) of vibrational displacement per unit time, a speed display (22) indicative of rotational speed, and a bearing condition display (20) indicative of bearing condition, all displays derived directly from the vibration transducer signal. The electrical signal is transformed (36) into a frequency spectrum that has an amplitude for each of a plurality of narrow frequency ranges or bins. Each frequency bin has a characteristic center frequency and a predefined width or band of frequencies. A speed analysis program (38) identifies a set of at least first, second and third order related frequency bins, i.e. frequency bins whose center frequencies are an even multiple of each other, that have a significantly high amplitude and provides the lowest bin center frequency as a control signal to the speed display. A bearing condition analysis program (40) eliminates the bins that are integer multiples of the running speed and lower frequency, e.g. less than third order, identifies sets of bins with relatively large amplitudes that are integer multiples of each other, and selects the set of bins with the largest amplitude as being controlling of bearing condition. After elimination of frequencies not indicative of bearing condition, the bearing defect frequency remains. The amplitude of this frequency is displayed on bearing condition readout (22). The amplitude indicating the severity of the bearing defect.

8 Claims, 13 Drawing Sheets

METHOD AND APPARATUS FOR ANALYZING ROTATING MACHINES

BACKGROUND OF THE INVENTION

The present invention relates to the art of analyzing and monitoring rotating machines. It finds particular application in conjunction with the analysis of vibration signals obtained from the rotating machine to produce a frequency spectrum from which a machine running speed and rolling element bearing condition is determined. It is to be appreciated, however, that the invention will also find application in other fields where the obtaining of a rotating object's speed is desired.

As is well known in the machine analysis and monitoring arts, defects in rotating machines can be analyzed through the use of a vibration frequency spectrum. The presence of vibration peaks at certain frequencies, which are known as defect frequencies, are indicative of a specific machine problem. As is shown in REFERENCE CHART 1 below, a common type reference used in the industry, defect frequencies are calculated as multiples of the running speed of the machine. For example, a machine rotor that is out of balance will generate a vibration at 1.0 times running speed of the machine, and a bent shaft will generate a vibration at 1.0 or 2.0 times running speed. Similarly, through calculation such as that of Equation 1 below, a rolling element bearing having a defective inner race can be found which may for example, generate a vibration at 5.63 times the running speed of the machine. Similar calculations are equally obtainable for the outer race defects as shown by Equation 2.

REFERENCE CHART 1 - VIBRATION SOURCES

| PROBABLE CAUSE | FREQUENCY relative to machine RPM | STROBE "PICTURE" | AMPLITUDE | NOTES |
|---|---|---|---|---|
| Unbalance | RPM × 1 | One - Steady | Radial - Steady | Most Common cause of vibration |
| Bent Shaft | RPM × 1 (or × 2) | 1, 2, or 3 | Axial - high | Strobe picture depends on machine usually unsteady |
| Sleeve Bearings | RPM × 1 | One - Steady | Shaft = Bearing Rdgs. | Compare shaft to bearing readings |
| Faulty Belts | RPM × 1 to RPM × 5 (Belt RPM × 2) | See "Notes" Column | Radial - Unsteady | Freeze belts with strobe and observe |
| Oil Whip | Less than machine RPM | Unstable | Radial - Unsteady sometimes severe | Frequency is near ½ RPM (commonly 42% to 48% × RPM) |
| Gears | High (related to number of gear teeth) | — | Radial - low | Use velocity or acceleration mode |
| Looseness | RPM × 2 | 2 | Proportional to looseness | Frequency coupled with misalignment |
| Foundation Failure | Unsteady | Unstable | Erratic | Shows up when balancing |
| Resonance | Specific "criticals" | 1 | High | Increased levels at critical speeds |
| Beat Frequency | Periodically varying | — | Pulsating | Caused by close RPM machines |
| Misalignment | | | | |
| Parallel | RPM × 1, × 2 | 1, 2, or 3 | Radial | Axial amplitude = .7 |
| Angular | RPM × 1, × 2 | 1, 2, or 3 | Axial - high | or higher of vertical or horizontal |

Equation 1:

$$IR = \frac{N}{2}\left(1 + \frac{d}{Pd}\cos\alpha\right)f_o$$

Equation 2:

$$OR = \frac{N}{2}\left(1 - \frac{d}{Pd}\cos\alpha\right)f_o$$

Where:
IR = Inner Race Defect
N = number of rotating elements
Pd = pitch diameter of rotating elements
OR = Outer Race Defect
d = diameter of rotating elements
$f_o$ = fundamental frequency of machine (Running Speed)

Therefore as can be seen from REFERENCE CHART 1 and Equations 1 and 2, machine analysis relies heavily on having an accurate knowledge of the machine's speed. A minor error in determining running speed would result in the inability to determine whether a specific examined frequency was truly a multiple of running speed, or a random frequency. In the prior art, obtaining the machine speed with the accuracy required was normally accomplished through the use of a speed sensor, see for example U.S. Pat. No. 4,426,641, METHOD AND APPARATUS FOR MONITORING THE SHAFT VIBRATION OF A ROTARY MACHINE, Kurihara, et al. Various means of speed sensing were used by the prior art including the rotary pulse gear 7 disclosed in FIG. 1c of Kurihara, et al.

Thus, due to the necessity of knowing a machine's speed accurately, a separate speed sensor in addition to a transducer, such as a vibration type, was required. The cost of separate speed and vibration sensors on a large machine such as a turbine-generator is no major problem. However, incorporating both a speed sensor and a vibration sensor on typical pumps, motors and fans does have a major impact. For example, in a typical refinery, chemical plant or other facility, literally thousands of machines may require monitoring. Installing a speed sensor on each of these machines significantly increases the installation costs and the maintenance costs of the monitoring equipment. Due to the increased costs for maintaining speed sensors on these machines, many machines which should be monitored are not.

Additionally, in the area of rolling element bearing defect analysis, two major problems exist. First, the amplitude of the vibration produced by the bearing defect is extremely small when compared to other vibrations produced in a rotating machine. Second, in order to calculate the bearing defect frequencies, the operator must know the specific geometry of the bearings, i.e. pitch diameter of the bearing, ball diameter in the bearing, number of balls in the bearing, and contact angle of the bearing, in addition to the running speed of the machine. Once the bearing has been installed within a machine, it is often impossible to ascertain the actual geometry of the bearing. Once installed in an operating machine, the parameters cannot be measured in a factory environment. Moreover, the machine records are often not detailed enough to reveal which specific bearing may be installed in any one of the many machines that are in service. As a complication, the manufacturer of standard machinery may buy the bearings from different manufacturers. Although the bearing fits the same machine, each commonly has different internal physical geometries.

Therefore, one of the drawbacks of prior art machine analysis and monitoring is a requirement of including hardware to maintain a separate speed sensing device in order to obtain an accurate determination of the running speed of the rotating machine.

Another drawback of the prior art systems which attempt to employ vibration signals to estimate rolling element bearing defects, is a requirement of knowing the specific geometry of the bearing which is being analyzed.

The present invention provides a new and improved method and apparatus for analyzing rotating machines which overcomes the above-referenced drawbacks and others. This satisfies a long-felt need in the industry to determine the running speed of a machine without the requirement of a separate speed transducer or sensor. Detailed frequency analysis is allowed on rotating machines with only an affixed vibration transducer.

SUMMARY OF THE INVENTION

In accordance with one aspect of the present invention, a method and apparatus is provided for determining the running speed of a rotating machine from a vibration signal obtained from the rotating machine.

More specifically, in the preferred embodiment a transducer attached to the rotating machine converts the vibration signal into an electrical signal. The electrical signal is filtered to obtain selected frequencies of the electrical signal. Thereafter, the filtered electrical signal is converted into a frequency spectrum through the use of a Fast Fourier Transform. Components of the frequency spectrum are defined as being characteristic of the running speed or as random, spurious, or caused by other effects. The components of the frequency spectrum which are random, spurious, or caused by other effects are eliminated. This allows the frequency components which are defined as representative of the running speed to be identified, to obtain a representative figure of the running speed. First, significant selected frequency peaks are defined within the frequency spectrum. Second, the significant peaks are refined to a resolution greater than the resolution of the spectrum based on a relationship of adjacent frequency bins to the defined frequency peaks. Third, the frequency peaks are resolved into sets which are at least first, second and third order related. Fourth, an estimated running speed is obtained from these sets. Fifth, the speed is confirmed from a running speed of a previously calculated value. Sixth, sets of frequency peaks of higher than third order are defined and compared with the confirmed estimated running speed. One of the higher order frequency peaks is selected based on the comparison as a representation or confirmation of the final running speed.

In accordance with another aspect of the present invention, a method and apparatus is provided for determining the condition of a rolling element bearing through the use of a vibration signal. A transducer which is attached to the rotating machine converts the vibration of the rotating machine into an electrical signal. The electrical signal is filtered to select frequency components of the electrical signal. The filtered electrical signal is transformed into a frequency spectrum and the running speed of the rotating machine is determined. The frequency spectrum is analyzed to identify the frequency components which are characteristic of problems other than bearing defects and these defects are then eliminated from the spectrum. Thereafter, the frequency component having the highest amplitude is selected.

A principle advantage of the present invention is the ability to calculate accurately the running speed of a rotating machine from a vibration signal produced by the machine.

Another advantage of the present invention resides in the elimination of the need for a separate speed transducer to calculate the running speed of the machine.

Still another advantage of the invention is found in the simplified manner of analyzing the condition of rolling element bearings without the need to have knowledge of specific bearing geometry information.

Still other advantages and benefits of the invention will become apparent to those skilled in the art upon a reading and understanding of the following detailed description.

BRIEF DESCRIPTION OF THE DRAWINGS

The invention may take form in various components and arrangements of components and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
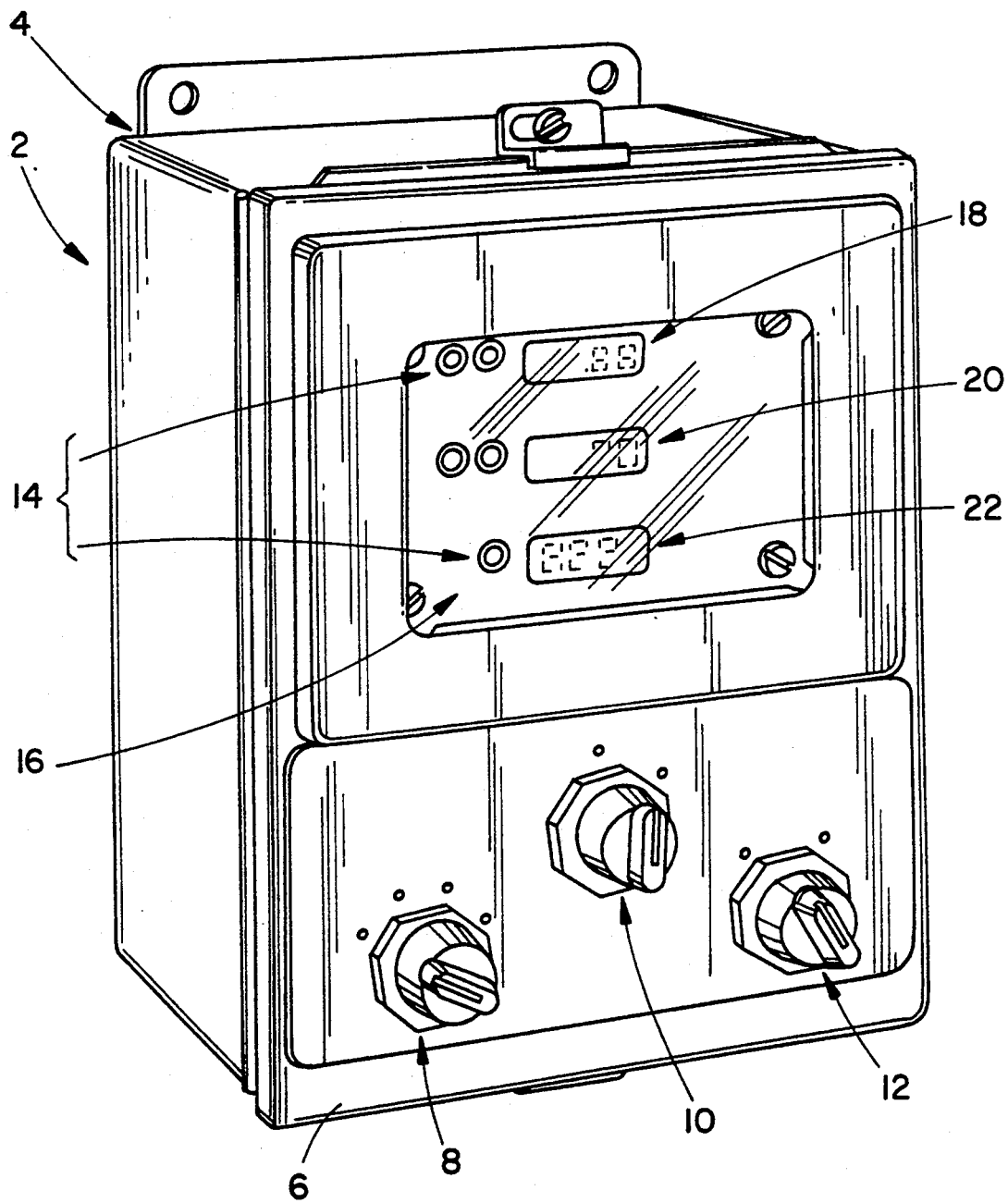
FIG. 1 is an illustration of the exterior of the present invention.

With reference to FIG. 1, a machine analysis device 2 is enclosed in a rugged outer casing 4 which is appropriate for industrial environments. Construction of the device can take form as both a permanently fixed device and a portable device. The front face 6 of the device contains various control switches 8, 10, and 12. Switch 8 selects the parameters to be displayed on the readouts 18, 20 and 22, and sets the machine such that when certain predetermined set points are detected by the machine, visible confirmation of the detection is shown through alarm indicators 14 located on a readout panel 16 of the device 2. Switch 10 controls operation of the device 2 between a normal mode and a reset mode. Switch 12 allows an operator to put the device in a run mode or a bypass system mode. An overall level display of the velocity of the vibrations (shown in inches per second), running speed (in RPM's) and bearings condition readings are displayed on the front of the device through readouts 18, 20 and 22, respectively.

Figure 2:
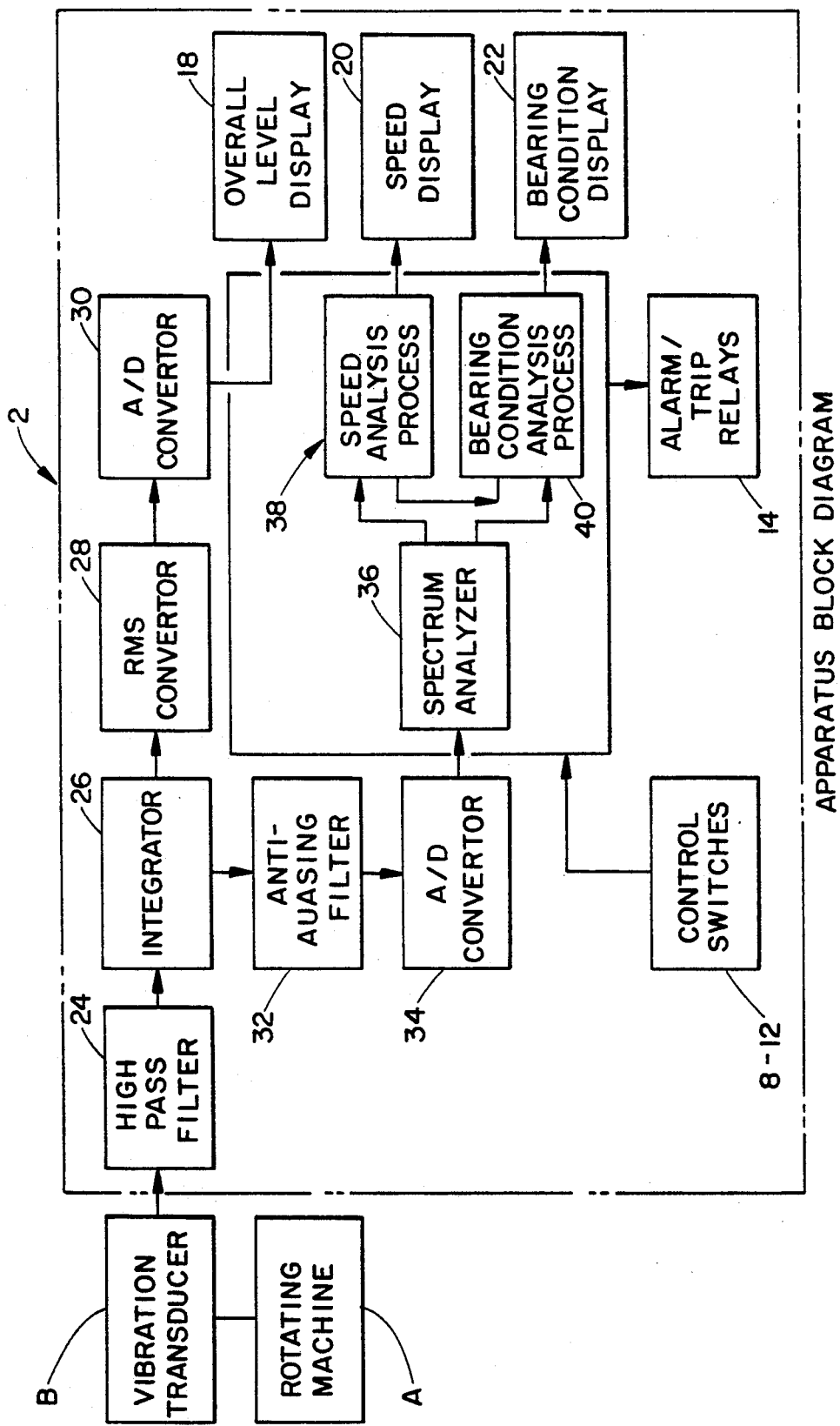
FIG. 2 is a block diagram of the apparatus connected with a transducer to a machine to be monitored or analyzed.

With reference to FIG. 2, a rotating machine A has a transducer or sensor, such as a vibration transducer B, mounted to a selected position on the machine. The vibration transducer B detects vibrations in the rotating machine A and converts those vibrations into proportional electrical signal components. The analysis device 2 has a high pass filter 24 which receives the vibration signal from the transducer B. The filter passes selected high frequencies and blocks low frequency vibrations not associated with machine condition, such as, ground vibrations, vibrations due to passing vehicles, etc. The passed high frequency signals are integrated by integrator 26 to convert the incoming vibration signal from one that is proportional to acceleration to one that is proportional to velocity.

The integrated signal is processed by a root-mean-square (RMS) converter 28 to provide an RMS signal that is proportional to average magnitude and independent of direction or sign. An A/D converter 30 digitalizes the RMS signal which is displayed digitally on overall level display 18. Preferably, the level is displayed in the units of inches per second to indicate total movement due to the vibration per unit time.

The integrated signal from the integrator 26 is also conveyed to an anti-aliasing filter 32 to filter out vibration frequencies higher than the highest frequency to be analyzed in the frequency spectrum. This step eliminates the possibility that a higher frequency vibration could take on the "alias" of a low frequency vibration, due to the inherent limitations of digital sampling techniques. Thereafter, the filtered signal is converted to a digital signal in an A/D converter 34. A 2,000 line spectrum analysis means 36 converts the digital integrated signal to a digital spectrum of a 0 to 1,000 Hz range with a 0.5 Hz resolution. Preferably, the spectrum analysis means performs a Fourier transform operation with Hanning weighting to emphasize side lobes of the frequency spectrums. The frequency spectrum is passed to a speed analysis means 38 wherein random or sporadic noise is eliminated, and components of the frequency not related to the rotating speed of the machine are eliminated to obtain an accurate estimation of the machine's running speed. A more detailed description of the speed analysis process 38 including the manner in which frequency components not related to the rotating speed are eliminated is presented in connection with FIGS. 3A and 3B. This running speed is then displayed on speed display 20.

The digital line spectrum from the spectrum analysis means 36 is passed to the bearing condition analysis process means 40. The bearing condition analysis process means generates information of an accurate estimation of the bearing condition from the speed analysis means 38 and the digital line spectrum. This estimation is displayed on the bearing condition display 22. A more detailed description of the process performed by the bearing condition analysis process means 40 is presented in conjunction with FIG. 9. The control switches 8, 10 and 12 and the alarms 14 are also shown in the block diagram.

Figure 3A:
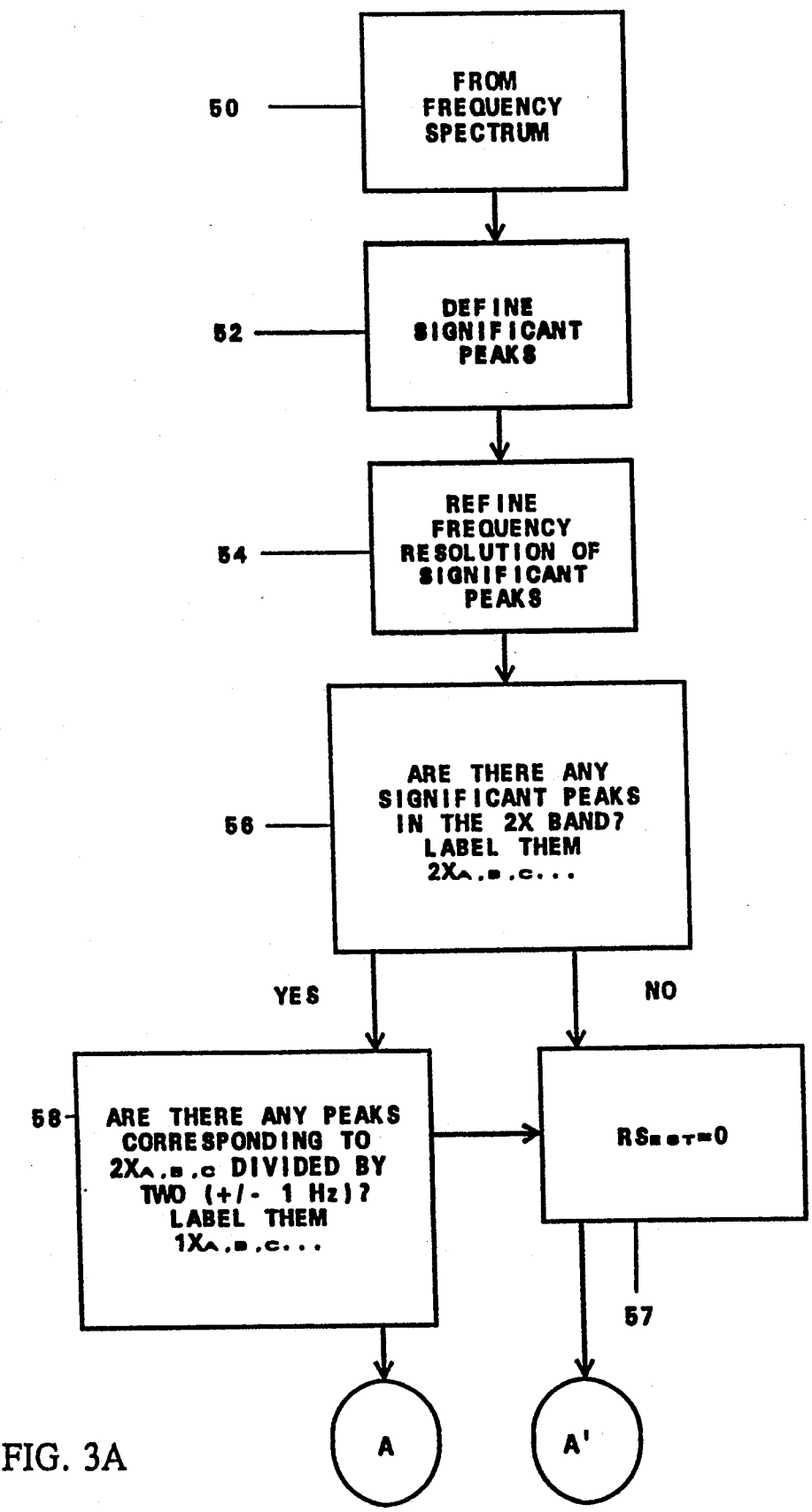
FIGS. 3A and 3B taken together are a block diagram showing the flow of the speed analysis process.
Figure 3A:
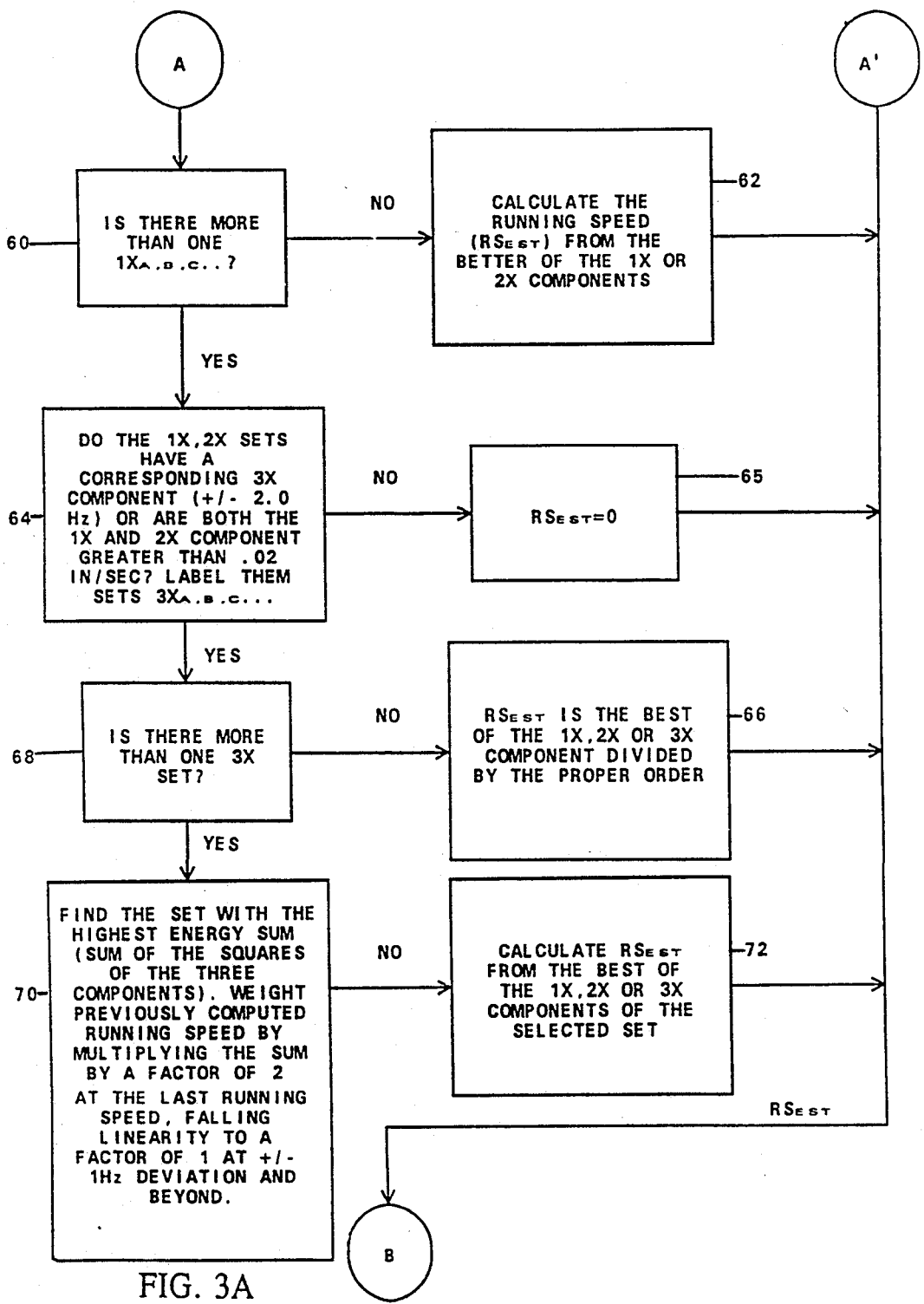
Figure 4:
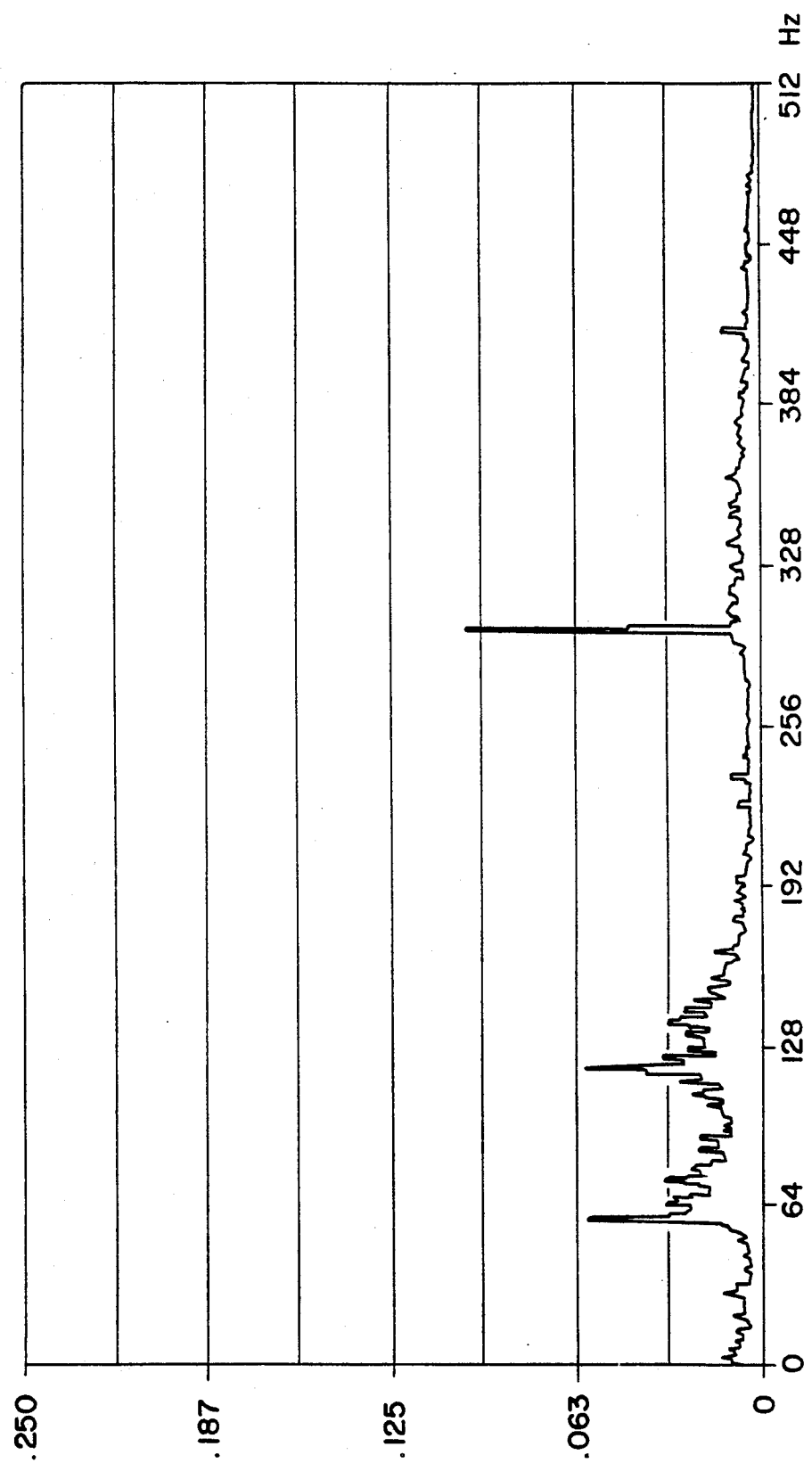
FIG. 4 is a graphic display of a frequency spectrum for a pump operating at approximately 3,550 RPM.

With reference to FIG. 3A, block 50 refers to a digital frequency spectrum from a 2,000 line spectrum with a 0 to 1,000 Hz range and 0.5 Hz resolution detailed from the spectrum analysis means 36. Such a spectrum analysis means produces an output representing the operation of a machine such as that shown in FIG. 4. This Figure is representative of a 512 Hz portion of a spectrum analysis of a pump running at approximately 3,550 RPM.

A step or means 52 defines peaks in the digital line spectrum which are to be used for further analysis and are designated as significant peaks. A significant peak is defined as a peak that reflects a velocity of vibration of 0.005 in/sec or greater, is at least as high as the next lower frequency bin and it is higher than the next higher frequency bin.

A step or means 54 refines the frequency peaks to improve upon the 0.5 Hz resolution or frequency bin width from the spectrum analysis means 36. The relationship used to define the exact frequency is:

$$F_{exact} = F_{ctr} +/- F_{bin} * 0.5 - \left( \frac{20 * \log_{10}(amp_0/amp_1)}{12} \right)$$

where:
$F_{exact}$ = the refined, exact calculated frequency,
$F_{ctr}$ = the nominal frequency of the selected bin,
$F_{bin}$ = a scaling factor in Hz/bin,
$amp_0$ = the amplitude of the selected bin,
$amp_1$ = the amplitude of the adjacent bin.

Figure 5:
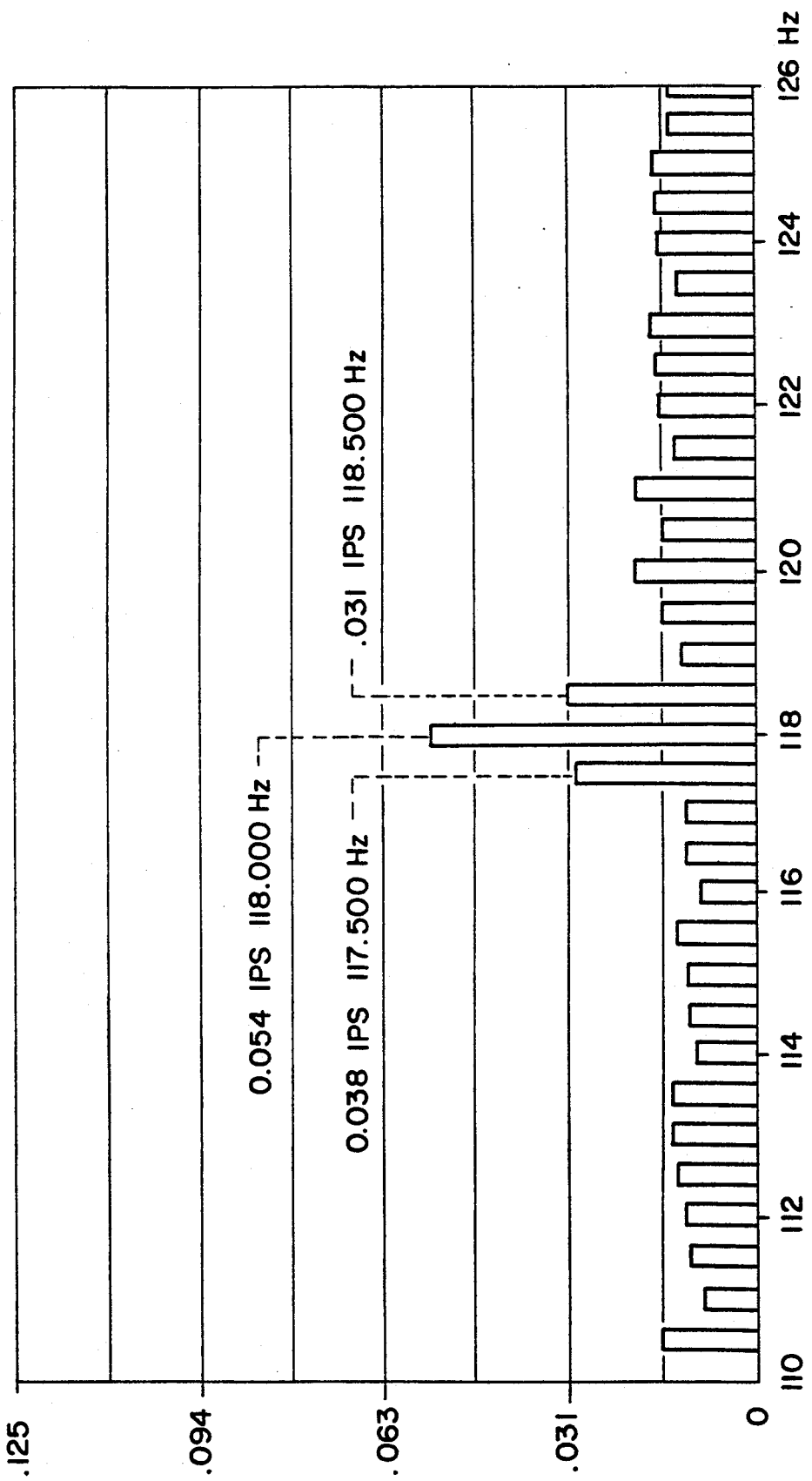
FIG. 5 is a graphic display of an expanded portion of a frequency spectrum illustrating a significant peak and refinement of the spectrum through calculation.

FIG. 5 shows an expanded portion of a frequency spectrum that illustrates both a significant peak, and an example of the refinement of the frequency by calculation using the above-noted relationship.

A step or means 56 defines any significant peaks in the 2x band, where the 2x band is defined as a band of frequencies that is between 20% less than two times a nominal speed setting and 10% more than two times the nominal speed setting. Thus, a nominal machine speed setting of 3,550 RPM (i.e. 3550 RPM÷60=59.16 Hz) would have a 2x band of 94.66 Hz to 130.15 Hz. The 2x band has been defined to allow for variance from the machines nominally rated speed and actual speed variances due to load or operating conditions. If no significant peaks are in the 2x band an estimated speed $RS_{est}$ is chosen as 0 as shown in step or means 57 and is transferred to a later part of the invention and persistence logic, which is explained later.

Figure 6:
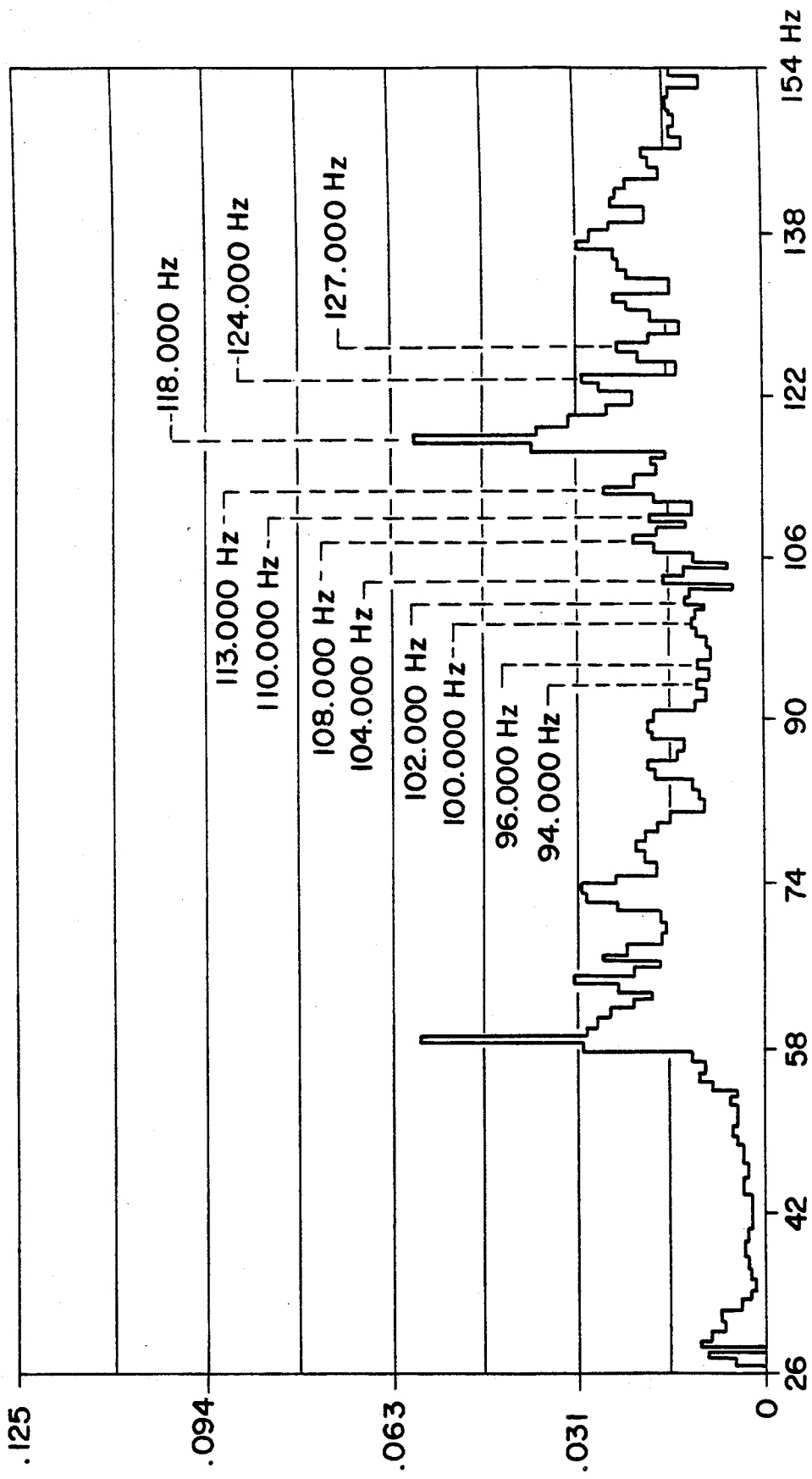
FIGS. 6 and 7 illustrate the manner in which significant peaks sets are built.
Figure 7:
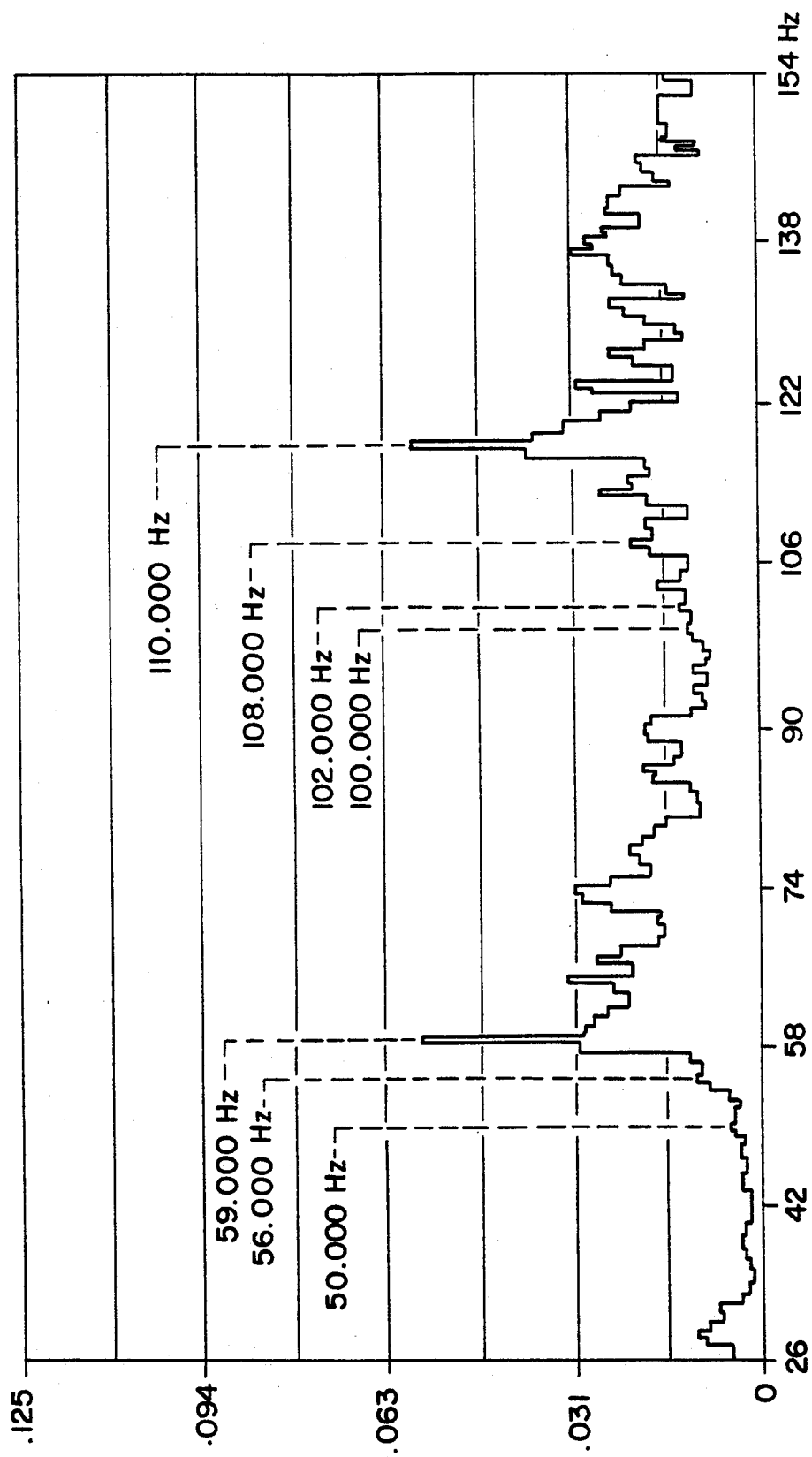

If significant peaks exist in the 2x band, sets of 1x and 2x peaks are built as in step or means 58. A 1x peak matches a 2x peak only if there is no peak closer to the 1x peak times two. The manner in which 1x and 2x peak sets are built is illustrated in FIGS. 6 and 7. Initially the significant peaks found in the 2x band of FIG. 6 are marked with their respective frequencies. The spectrum is then analyzed for the existence of frequencies that are representative of the 1x component of the defined 2x frequencies. Corresponding 1x components are defined as the 2 x frequency component divided by two, $+/-1$ Hz. In FIG. 7, the frequencies that are considered the corresponding 1x components of the 2x components as defined in FIG. 6 are illustrated. FIG. 7 also illustrates the four potential 1x, 2x sets existing in this particular situation, namely:

| 2x component | corresponding 1x component |
| --- | --- |
| 100 Hz. | 50 Hz. |
| 102 Hz. | 50 Hz. |
| 108 Hz. | 55 Hz. |
| 118 Hz. | 59 Hz. |

Due to the specified $+/-1$ Hz. tolerance used when defining the matching 1x components, the 50 Hz. frequency could represent the 1x component of either the 100 Hz. or 102 Hz., 2x frequency. Thusly, step or means 58 also defines a 1x peak as matching a 2x peak only if there is not a peak closer to the 1x peak times two. By definition then, the 50 Hz. component in FIG. 7 can only be associated with the 100 Hz., 2x peak and not the 102 Hz., 2x peak.

If there is only one set of corresponding peaks of 1x and 2x bands, an estimated running speed $RS_{est}$ is calculated from the better of the 1x or 2x peaks by step or means 60 and 62 by dividing the 1x or 2x peak by its respective order. "Better" is defined as:

If the 2x peak is present, and is at least $\frac{1}{2}$ the amplitude of the 1x peak, and its surroundings do not indicate interference with its Hanning skirt (the sum of the bins on either side of the center frequency do not exceed the center frequency by more than a selected tolerance), then the 2x peak is used.

Otherwise the 1x peak is used.

If more than one corresponding sets of peaks in the 1x and 2x bands are defined by step or means 58, then step or means 64 looks for a peak in a three times the nominal operating speed band (3x) to verify the correspondence among the 1x and 2x band peaks. The step or means 64 does not eliminate the 1x and 2x peak set if a corresponding 3x peak is not found as long as the 1x and 2x peaks are strong (greater than or equal to 0.02 in/sec). If neither the 1x or 2x peak is above 0.02 in/sec, nor is there a 3x corresponding peak (within $+/-2.0$ Hz), then the estimated speed $RS_{est}$ is set to 0 by step or means 65, and passed on to the persistence section.

If only one matching 3x band peak is identified by the step or means 64, the process uses an estimated speed $RS_{est}$ that is the best of the 1x, 2x or 3x components as decided by a step or means 66. In this case, "best" is defined as follows:

If the 3x peak is present, and is at least $\frac{1}{2}$ the amplitude of the 2x peak, and its surroundings do not indicate interference with its Hanning skirt (the bins on either side of the center frequency do not add up to significantly more than the center frequency), then the 3x peak is be used.

Otherwise, if the 2x peak is present and its surroundings do not indicate interference with its Hanning skirt, the 2x peak is used.

Otherwise, the 1x peak is used.

Figure 8:
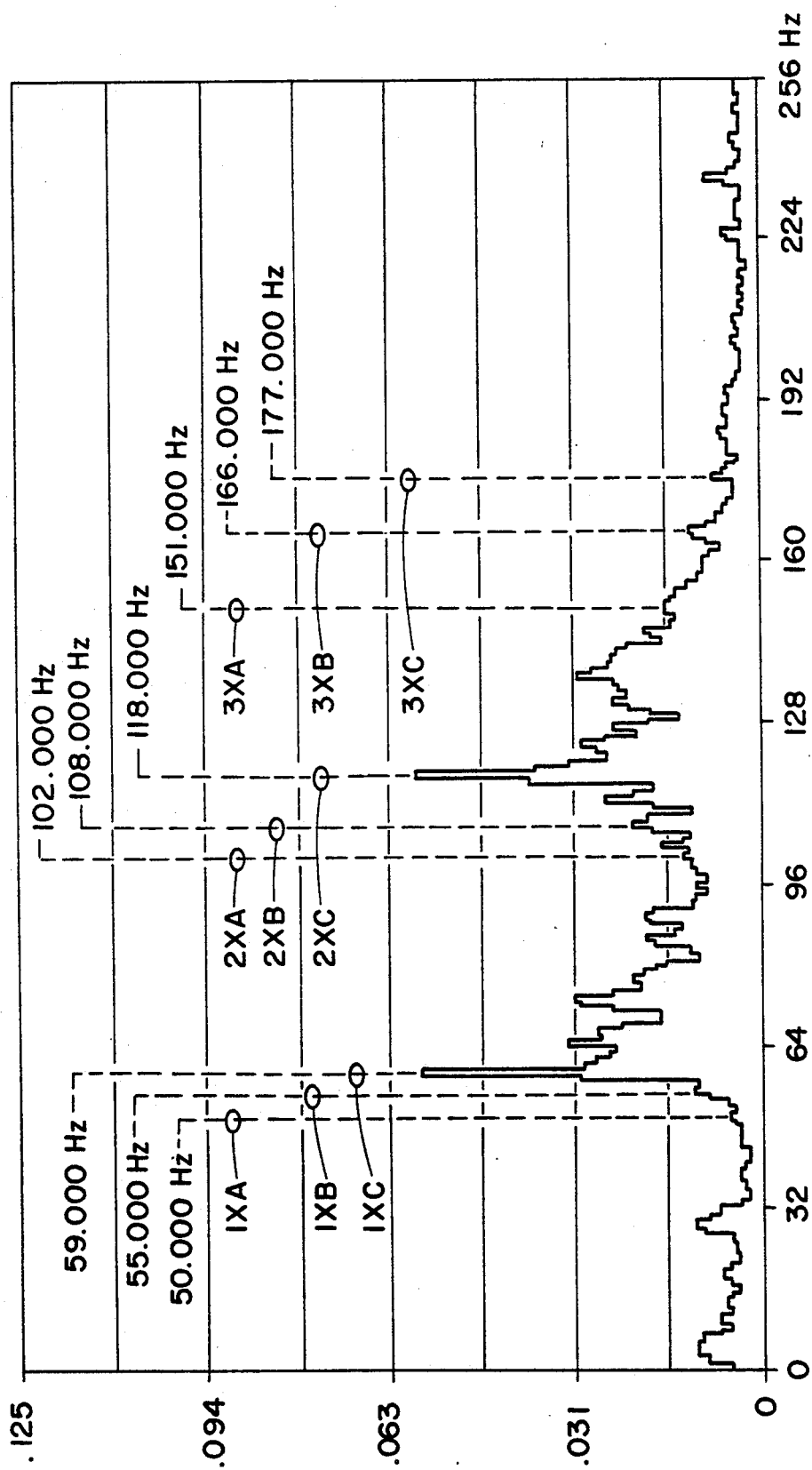
FIG. 8 graphically illustrates the functions of steps or means 68, 70, and 72 of the present invention.

If more than one set of matching 1x, 2x and 3x peaks is detected by step or means 68, a step or means 70 determines which peak set to use to calculate the estimated running speed $RS_{est}$. When multiple peak sets exist, the set with the highest energy sum is selected as the best set of 1x, 2x and 3x components to use for estimated running speed $RS_{est}$ calculations. Energy sums are weighted to give preferential treatment to sets closest to the last determined final running speed. The estimated running speed, $RS_{est}$ is calculated by dividing the "best" 1x, 2x or 3x component of the "best" 1x, 2x and 3x set by the respective order. The "best" 1x, 2x or 3x component is defined as described previously. This estimated running speed $RS_{est}$ is passed on to the persistence logic as before. FIG. 8 illustrates the function of steps or means of 68, 70 and 72. The 1x, 2x peak sets defined in FIG. 8 are further refined by the presence of peaks that represent the 3x component of these sets. FIG. 8 shows that these 1x, 2x and 3x peak sets are labeled $1x_A$, $2x_A$, and $3x_A$; $1x_B$, $2x_B$, and $3x_B$; etc. Step or means 70 selects the best of these 1x, 2x and 3x sets by their energy sum content as previously described. Thus, as can graphically be seen in FIG. 8, the 59 Hz., 118 Hz., and 177 Hz. set would be used to calculate the estimated running speed $RS_{est}$.

Figure 3B:
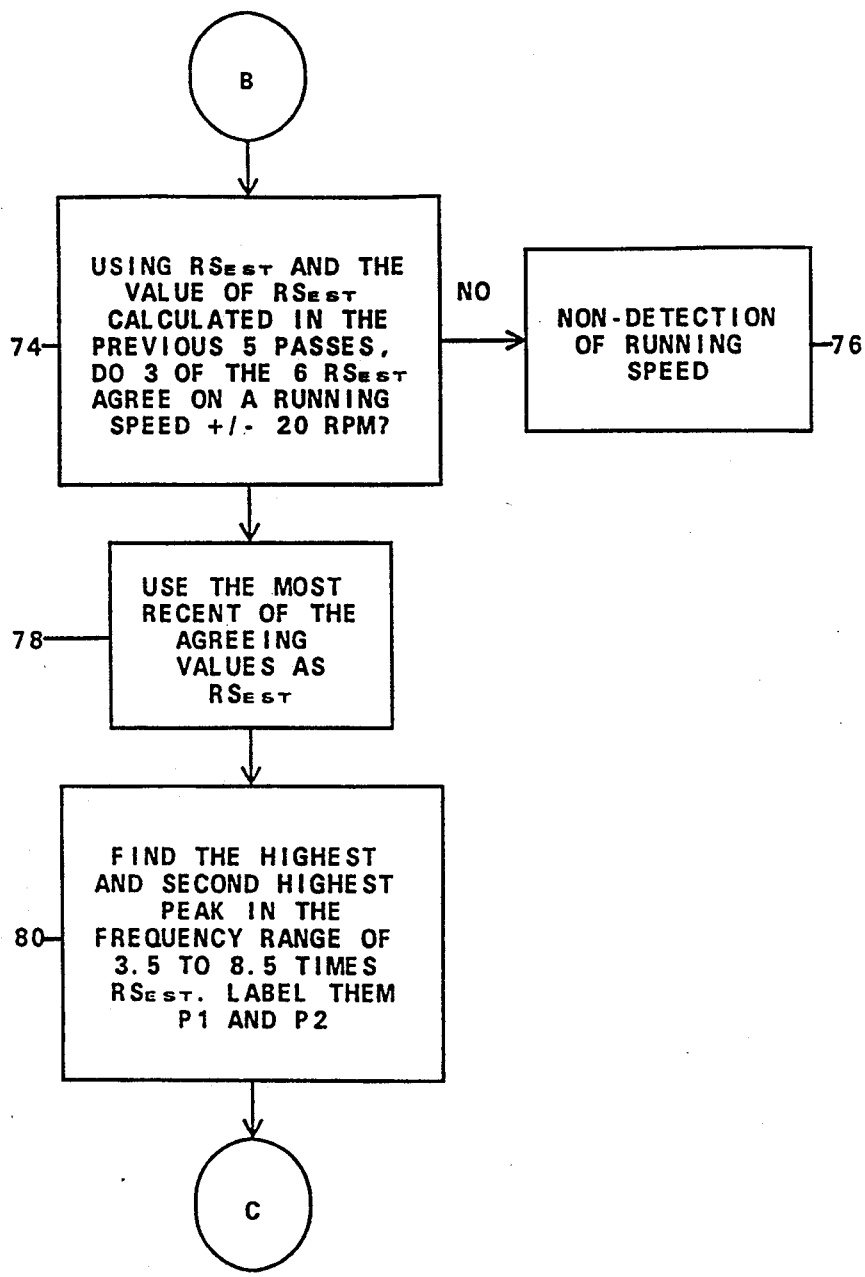
Figure 3B:
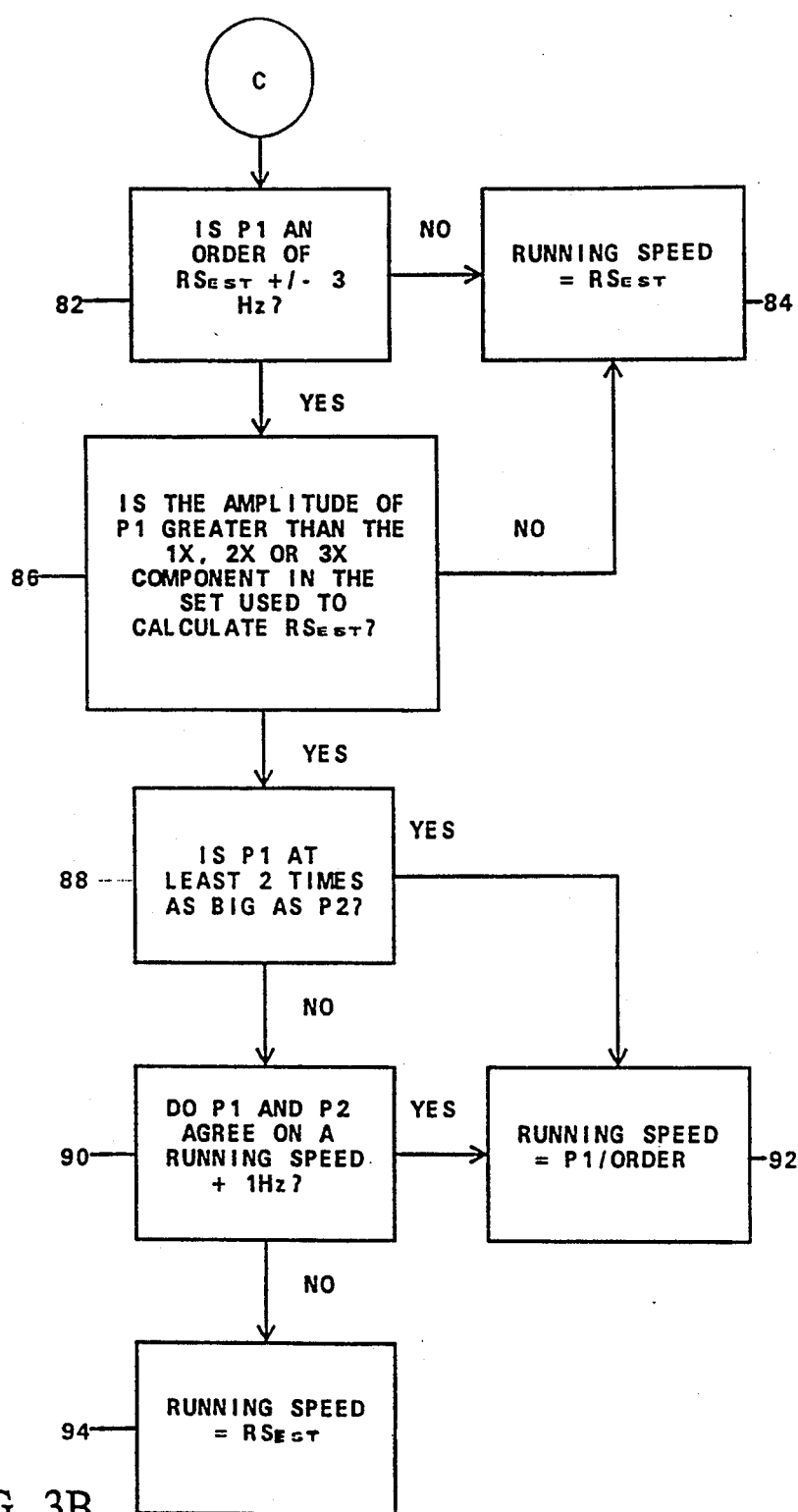

With reference to FIG. 3B, which is the beginning of the "persistence" logic, the speed analysis process 38 uses the estimated running speed $RS_{est}$ as an input to the persistence logic for determining and verifying a final running speed $RS_{final}$. Persistence logic allows the running speed components of vibration to not be detected for a period of time, without causing the system to lose the running speed. A step or means 74 compares the currently calculated $RS_{est}$ with a previously determined final running speed $RS_{final}$ to see if they match within $+/-20$ RPM. If a preselected fraction, (e.g. three (3) of the last six (6) $RS_{est}$) do not agree within $+/-20$ RPM, the process logs this cycle in block 76 as a nondetection of running speed and starts again. If the preselected fraction of the estimated running speeds $RS_{est}$ do agree, the process follows to step or means 78 and uses the most recent $RS_{est}$ as the estimated running speed for further calculations. If the new estimated running speed is 0, or drastically different than previously calculated speeds, the process uses the old calculated speed for a period of time until the speed returns to the previously calculated speed range or settles on a new steady speed.

After determining the estimated running speed $RS_{est}$ in step or means 74, the process proceeds to higher order vibrations, if present, to further corroborate $RS_{est}$ or define a more accurate final running speed. Higher order vibrations, if present, yield an even more accurate final running speed than the 1x, 2x or 3x components, when the higher order vibrations are divided by their order.

A step or means 80 looks for possible matching higher order vibrations in the 3.5 times to 8.5 times range. The highest two peaks in the 3.5 times to 8.5 times range are found, and labeled P1 (highest) and P2 (next highest). P1 is then investigated by step or means 82 to determine whether it is an integer order (multiple) of the estimated running speed $RS_{est}$, $+/-3$ Hz. If it is not, then the estimated running speed $RS_{est}$ is sent to a step or means 84 and designated as a final running speed $RS_{final}$. If P1 is an order of the estimated running speed $RS_{est}$, then P1 is investigated by step or means 86 to determine whether it is strong enough to be used as a higher order multiple of the estimated running speed $RS_{est}$ for calculating the final running speed $RS_{final}$. In this case "strong enough" is defined as bigger in amplitude than either the 1x, 2x, or 3x components in the set used to calculate $RS_{est}$. If P1 is not this strong, then the estimated running speed $RS_{est}$ is designated as the final running speed $RS_{final}$ by the step or means 84.

If P1 is this strong, a step or means 88 further verifies its relationship with the second highest peak in the 3.5x to 8.5x range P2. If P1 is at least two times as big as P2, it is used to calculate the final running speed $RS_{final}$. If P1 is not at least two times as big as P2, but step or means 90 determines that they both agree on a running speed within 1 Hz, then a step or means 92 divides P1 by its order to calculate the final running speed $RS_{final}$.

If P1 and P2 do not agree on a running speed within 1 Hz, then the estimated running speed $RS_{est}$ is designated as the final running speed by step or means 94. The end result of the running speed logic program is a running speed calculation that is equal to or better than many running speeds obtained with speed sensors.

Once the running speed of the machine being analyzed has been obtained, this speed can also be used to calculate the condition of the rolling element bearings within the machine.

Figure 9:
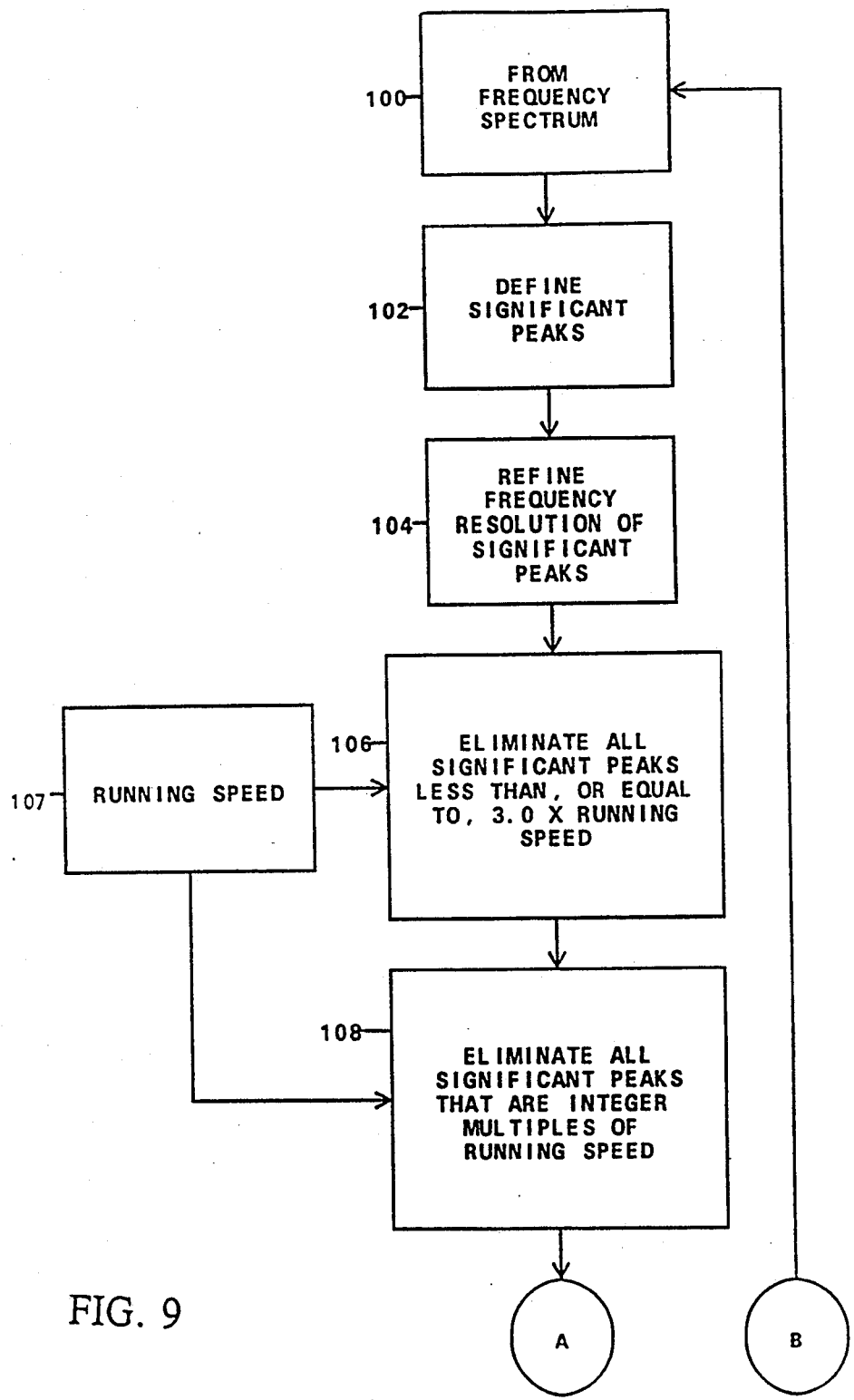
FIG. 9 is a block diagram showing the flow of the bearing condition analysis process.
Figure 9:
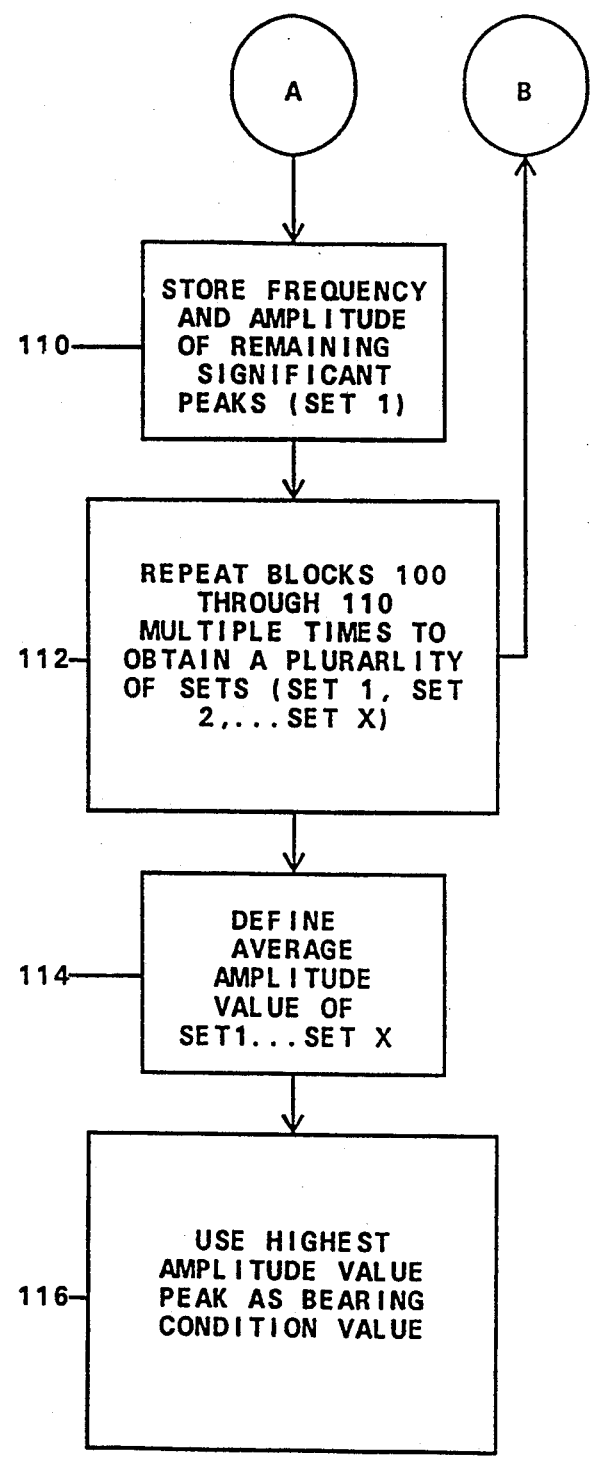

With reference to FIG. 9, the bearing condition analysis means 40 receives the digital line spectrum data from the spectrum analysis means 36 with a step or means 100.

A step or means 102 defines significant peaks in the spectrum for further analysis. A significant peak being defined similarly as to that in conjunction with step or means 52, as a peak that is 0.005 in/sec or greater, is at least as high as the next lower frequency bin and is higher than the next higher frequency bin.

A step or means 104 refines the frequency peaks to improve upon the 0.5 Hz resolution from the spectrum analysis means 36 analogous to step or means 54.

The bearing condition process uses the machine running speed to define significant peaks as orders (multiples) of running speed 107. The bearing condition process then uses the running speed data to eliminate frequencies from the digital line spectrum 100 that could not be caused by defective bearings. The remaining values are then examined, and the highest amplitude value is used as a bearing condition indicator.

More specifically, a step or means 106 eliminates all low order significant peaks that are equal to, or less than a preselected multiple of, e.g. 3.0 times the final running speed. This operation eliminates potential machine defect frequencies such as, unbalance, misalignment, and looseness. This operation also eliminates the vibration energy associated with pump cavitation from the spectrum.

A step or means 108 eliminates all integer multiples of running speed. This leaves frequency peaks caused by bearing defects and/or possibly sporadic or random peaks. The step or means 106 and 108 removes peaks attributable to the previously calculated running speed and multiples thereof to eliminate unnecessary peaks.

Steps or means 110 and 112 store the frequency and amplitude of the remaining significant peaks and institute a loop process to gather multiples of sets of corresponding peaks. A step or means 114 reduces the random or sporadic peaks from the spectrum by averaging corresponding peak amplitude values. A step or means 116 identifies the frequency with the highest average peak value or amplitude as being reflective of a defect in the bearing.

The frequencies remaining following step or means 116 is the bearing defect frequency. The amplitude of the remaining frequency is thereafter displayed on the bearing readout 22 of device 2. The amplitude figure of the bearings readout 22 is an indication of the severity of the bearing defect (i.e. the higher the amplitude readout the greater the severity of defect).

The invention has been described with reference to the preferred embodiment. Obviously, alterations and modifications will be apparent to those of ordinary skill in the art upon reading and understanding the preceding specification. It is intended that the invention be construed as including all such alterations and modifications in so far as they come within the scope of the appended claims or the equivalents thereof.

What is claimed is:

1. A method for determining a running speed of a rotating machine whose rotating elements are enclosed in a housing, the method comprising:

sensing, from a vibration transducer input means in contact with said housing, mechanical vibrations of the rotating machine;

converting the sensed vibrations into an electrical signal;

filtering the electrical signal to obtain and select frequencies of the electrical signal;

converting the filtered electrical signal into a frequency spectrum;

selecting frequency components of the frequency spectrum characteristic of the running speed, and components that are random, spurious and caused by other effects;

eliminating the components that are random, spurious and caused by other effects;

calculating the running speed from the selected running speed characteristic frequency components.

2. The method of claim 1 wherein the step of selecting the frequency components includes:

identifying frequency peaks within the frequency spectrum;

identifying corresponding first, second, and third order sets of the frequency peaks;

identifying corresponding frequency peaks of greater than the third order;

and wherein the calculating step includes:

calculating an estimated running speed from a one of the first, second, and third order related sets;

confirming the estimated running speed with a previously calculated final running speed;

comparing the confirmed estimated running speed with a running speed corresponding to the greater than third order frequency peaks;

selecting one of the greater than third order frequency peak running speed and the estimated running speed, as a representation of the final running speed.

3. An apparatus for determining running speed of a rotating machine whose rotating elements are enclosed in a housing, the apparatus comprising:

a vibration transducer input means in contact with said housing for converting sensed mechanical vibrations into an electrical signal;

an analog-to-digital convertor means for converting the electrical signal into a digital signal;

a transform means for transforming the digital signal into a frequency spectrum;

a selecting means for selecting frequency components of the frequency spectrum characteristic of running speed and frequency components that are random, spurious and caused by other effects;

an eliminating means for eliminating the frequency components that are random, spurious and caused by other effects;

a converting means for converting the selected running speed characteristic frequency components to obtain an indication of the running speed.

4. The apparatus of claim 3 wherein the selecting means includes:

a refining means for selectively combining portions of each selected components with adjacent frequency components to resolve the selected components into a greater number of frequency components each with a narrower frequency range;

an identifying means for identifying sets of the refined frequency components that are first, second and third order related as having center frequencies that are even multiples of each other;

a running speed estimating means for estimating an estimated running speed from the center frequencies of one of the first, second, and third order related sets;

a confirming means for confirming the estimated running speed with a previously known final running speed;

means for identifying a set of higher order frequency components related to the first, second and third order related sets, the higher order frequency component sets having a higher frequency greater than the third order related set;

comparing means for comparing the confirmed estimated running speed with the higher order frequency components of the higher order frequency component set;

selecting means for selecting one of the higher order frequency components and the estimated running speed, as a representation of the final running speed.

5. A method for determining a running speed of a rotating machine from a sensed vibration of the rotating machine, the method comprising:

converting the sensed vibration into an electrical signal;

filtering the electrical signal to obtain and select frequencies of the electrical signal;

converting the filtered electrical signal into a frequency spectrum;

selecting frequency components of the frequency spectrum characteristic of the running speed, and components that are random, spurious and caused by other effects by, identifying frequency peaks within the frequency spectrum, identifying corresponding first, second, and third order sets of the frequency peaks, and identifying corresponding frequency peaks of greater than the third order;

eliminating the components that are random, spurious and caused by other effects;

calculating the running speed from the selected running speed characteristic frequency components by, calculating an estimated running speed from at least a one of the first, second, and third order related sets, and confirming the estimated running speed with a previously calculated final running speed;

comparing the confirmed estimated running speed with a running speed corresponding to the greater than third order frequency peaks;

selecting one of the greater than third order frequency peak running speed and the estimated running speed, as a representation of the final running speed.

6. An apparatus for determining running speed of a rotating machine from sensed vibrations, the apparatus comprising: p1 a vibration detector means for converting the sensed vibrations into an electrical signal;

an analog-to-digital convertor means for converting the electrical signal into a digital signal;

a transform means for transforming the digital signal into a frequency spectrum;

a selecting means for selecting frequency components of the frequency spectrum characteristic of running speed and frequency components that are random, spurious and caused by other effects;

an eliminating means for eliminating frequency components that are random, spurious and caused by other effects;

a refining means for selectively combining portions of each selected components with adjacent frequency components to resolve the selected components into a greater number of frequency components each with a narrower frequency range;

an identifying means for identifying sets of the refined frequency components that are first, second and third order related as having center frequencies that are even multiples of each other;

a running speed estimating means for estimating an estimated running speed from the center frequencies of one of the first, second, and third order related sets;

a confirming means for confirming the estimated running speed with a previously known final running speed;

means for identifying a set of higher order frequency components related to the first, second and third order related sets, the higher order frequency component sets having a higher frequency greater than the third order related set;

comparing means for comparing the confirmed estimated running speed with the higher order frequency components of the higher order frequency component set; and, selecting means for selecting one of the higher order frequency components and the estimated running speed, as a representation of the final running speed.

7. A method for determining a running speed of a rotating machine enclosed within a housing, the method comprising:

sensing mechanical vibrations of the rotating machine with a vibration detector in contact with the housing of the rotating machine;

converting the sensed mechanical vibrations into an electrical signal;

filtering the electrical signal to obtain and select frequencies of the electrical signal;

converting the filtered electrical signal into a frequency spectrum ranging approximately from 0 Hz to 1000 Hz.

selecting frequency peaks of the frequency spectrum ranging from about 0 Hz to about 1000 Hz characteristic of the running speed, and components that are random, spurious and caused by other effects;

eliminating the components that are random, spurious and caused by other effects;

calculating an estimated running speed from at least one of the frequency peaks;

confirming the estimated running speed with a previously calculated final running speed;

comparing the confirmed estimated running speed with a running speed corresponding to a highest obtained frequency peak of the frequency peaks; and, selecting one of the highest obtained frequency peak representing the running speed and the estimated running speed, as a representation of the final running speed.

8. An apparatus for determining running speed of a rotating machine enclosed within a housing, the apparatus comprising:

a vibration detector means in contact with the housing for converting sensed mechanical vibrations into an electrical signal;

an analog-to-digital convertor means for converting the electrical signal into a digital signal;

a transform means for transforming the digital signal into a frequency spectrum ranging approximately from 0 Hz to 1000 Hz;

a selecting means for selecting frequency peaks of the frequency spectrum characteristic of running speed and frequency components that are random, spurious and caused by other effects;

an eliminating means for eliminating the frequency components that are random, spurious and caused by other effects;

a running speed estimating means for estimating an estimated running speed from center frequencies of at least one of the frequency peaks;

a confirming means for confirming the estimated running speed with a previously known final running speed;

means for identifying a highest obtained frequency peak of the frequency peaks;

comparing means for comparing the confirmed estimated running speed with the highest obtained frequency peak; and, selecting means for selecting one of the highest frequency peak and the estimated running speed, as a representation of the final running speed.

* * * * *